(12) United States Patent
Endo et al.

(10) Patent No.: US 8,791,126 B2
(45) Date of Patent: Jul. 29, 2014

(54) 2-ALKYNYL-N9-PROPARGYLADENINE AND MEDICINAL USE THEREOF

(75) Inventors: Kazuki Endo, Choshi (JP); Kohei Yamada, Choshi (JP); Kazuki Deguchi, Choshi (JP)

(73) Assignee: Yamasa Corporation, Choshi-shi (JP)

( * ) Notice: Subject to any disclaimer, the term of this patent is extended or adjusted under 35 U.S.C. 154(b) by 0 days.

(21) Appl. No.: 13/989,647

(22) PCT Filed: Nov. 24, 2011

(86) PCT No.: PCT/JP2011/076984
§ 371 (c)(1),
(2), (4) Date: May 24, 2013

(87) PCT Pub. No.: WO2012/070601
PCT Pub. Date: May 31, 2012

(65) Prior Publication Data
US 2013/0245046 A1    Sep. 19, 2013

(30) Foreign Application Priority Data
Nov. 24, 2010  (JP) .................. 2010-260729

(51) Int. Cl.
*C07D 473/34*    (2006.01)

(52) U.S. Cl.
USPC .............. 514/263.23; 514/26.4; 544/277

(58) Field of Classification Search
CPC .................................. C07D 473/34
See application file for complete search history.

(56) References Cited

U.S. PATENT DOCUMENTS

| 5,484,920 | A | 1/1996 | Suzuki et al. |
| 5,587,378 | A | 12/1996 | Suzuki et al. |
| 6,841,549 | B1 | 1/2005 | Asano et al. |

FOREIGN PATENT DOCUMENTS

| JP | 6 211856 | 8/1994 |
| JP | 11 263789 | 9/1999 |
| JP | 2005 500355 | 1/2005 |
| JP | 2007 531729 | 11/2007 |
| JP | 2010 505747 | 2/2010 |
| WO | 01 02400 | 1/2001 |

OTHER PUBLICATIONS

Mihara, T. et al., "Pharmacological Characterization of a Novel, Potent Adenosine $A_1$ and $A_{2A}$ Receptor Dual Antagonist, 5-[5-Amino-3-(4-fluoropheny)pyrazin-2-yl]-1-isopropylpyridine-2(1H)-one(ASP5854), in Models of Parkinson's Disease and Congnition", The Journal of Pharacology and Experimental Therapeutics, vol. 323, No. 2, pp. 708-719, Aug. 7, 2008).

Ongini, E. et al., "Pharmacology of adenosine $A_{2A}$ receptors", Trends in Pharmacological Sciences, vol. 17, No. 10, pp. 364-372, (Oct. 1996).

Matsunaga, H. et al., "Synthesis and structure-activity relationships of $N^9$-alkyl-2-alkynyladenine derivatives as $A_{2A}$ adenosine receptor antagonists", The 30th Medicinal Chemistry Symposium Abstract, The Pharmaceutical Society of Japan Division of Medicinal Chemistry, Pages (Total 3 Pages), (2012).

International Search Report Issued Dec. 27, 2011 in PCT/JP11/076984 filed Nov. 24, 2011.

*Primary Examiner* — Anna Pagonakis
(74) *Attorney, Agent, or Firm* — Oblon, Spivak, McClelland, Maier & Neustadt, L.L.P.

(57) ABSTRACT

In the present invention, a novel 2-alkynyl-N9-propargyladenine represented by formula (I)

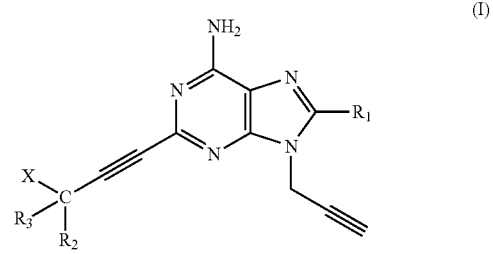

wherein $R_1$ represents a halogen atom, a furyl group, or a triazolyl group; $R_2$ and $R_3$ each represents a hydrogen atom or a C1-8 alkyl group, or form a cycloalkyl group by bonding to each other; and X represents a hydrogen atom or a hydroxyl group, or a pharmaceutically acceptable salt thereof, has a stronger and longer-lasting effect as a therapeutic agent for Parkinsonian syndromes.

11 Claims, 7 Drawing Sheets

2-ALKYNYL-N9-PROPARGYLADENINE AND MEDICINAL USE THEREOF

TECHNICAL FIELD

The present invention relates to a novel 2-alkynyl-$N^9$-propargyladenine and pharmaceutical use thereof. More specifically, the present invention relates to a 2-alkynyl-$N^9$-propargyladenine represented by the following formula (I):

[Formula 1]

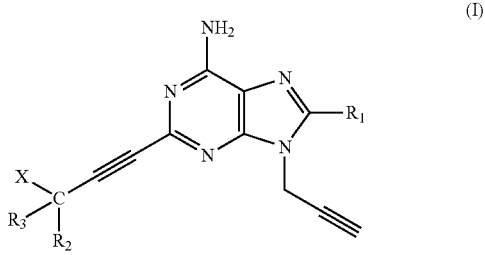

wherein $R_1$ represents halogen, a furyl group or a triazolyl group; $R_2$ and $R_3$ each represent hydrogen or an alkyl group having 1 to 8 carbon atoms, or $R_2$ and $R_3$ represent a cycloalkyl group in which $R_2$ and $R_3$ are linked together; and X represents hydrogen or a hydroxyl group, or a pharmaceutically acceptable salt thereof, which acts as an adenosine $A_{2a}$ receptor antagonist, and pharmaceutical use thereof.

BACKGROUND ART

Parkinson's disease (shaking palsy) is a brain disease characterized by tremors (trembling or vibrating) of the body, as well as difficulties in walking, movements, and coordination.

The development of Parkinson's disease is related to a damage of a part of the brain which controls the muscular movements. Dopaminergic cells, which are concentrated in the relevant part of the substantia nigra, are the most rapidly aging cells in the body, and denaturation of dopamine-producing cells causes a reduction in the production of dopamine and impairs the control of movement, thus developing Parkinson's disease.

Symptoms very similar to Parkinson's disease as mentioned above are known to be also caused by various other causes, such as Encephalitis lethargica, cerebral arteriosclerosis, intoxication with drugs/carbon monoxide/manganese/cyanide compounds or the like, brain tumor, after a head injury, or syphilis. Including these, a condition in which symptoms such as muscle stiffness, tremor, or akinesia occur in different combinations is called "Parkinson's syndrome".

No radical therapeutic methods are known for Parkinson's syndrome, and conventional therapeutic methods have been aimed at controlling the symptoms. Representative therapeutic methods include a method of administering to a patient L-DOPA, which is a precursor of dopamine, singly or in combination with another drug. However, when this therapeutic method is conducted for a long time period, the efficacy of L-DOPA tends to lower over time, and actually patients who received a chronic treatment with L-DOPA had a problem in that the aforementioned symptoms often became severe in addition to occurrence of other adverse reactions due to neurotoxicity intrinsic to L-DOPA.

On the other hand, adenosine is known to be an endogenous modulator of many physiological functions. It has been revealed that the action of adenosine is mediated by an interaction with different membrane specific receptors which belong to the family of G-protein coupled receptors present on the cell surface, and there are at least 4 subtypes of adenosine receptors, $A_1$, $A_{2a}$, $A_{2b}$, and $A_3$.

In recent years, the role of adenosine as a neurotransmitter, its receptors, and their functional properties have been discovered, and thereby it has been revealed that an antagonist of adenosine $A_{2a}$ receptor can be used as a therapeutic agent for movement disorder accompanied by Parkinson's syndrome (Patent Literatures 1 to 3).

CITATION LIST

Patent Literature

Patent Literature 1: JP 6-211856 A
Patent Literature 2: JP 2007-531729 A
Patent Literature 3: JP 2010-505747 A
Patent Literature 4: JP 11-263789 A

SUMMARY OF INVENTION

Technical Problem

However, although an adenosine $A_{2a}$ antagonist described in Patent Literature 1, 8-[(E)-2-(3,4-dimethoxyphenyl)vinyl]-1,3-diethyl-7-methyl-3,7-dihydro-1H-purin-2,6-dione (hereinafter referred to as "KW-6002") is known, which has conventionally been considered as promising as a therapeutic agent for Parkinson's syndrome, it cannot be said that sufficient comparison is conducted with an adenine derivative which differs in fundamental structure of the skeleton such as the compound of the present invention.

Patent Literatures 2 to 4 disclose an adenosine $A_{2a}$ receptor antagonist compound having adenine as a basic skeleton; however, these do not disclose the compound of the present invention as a specific compound, including the synthesis method thereof.

To describe more specifically, Patent Literatures 2 and 3 disclose an adenosine $A_{2a}$ receptor antagonist having adenine as a basic skeleton. However, Patent Literature 2 never discloses the compound of the present invention, including the synthesis method thereof. In addition, as shown in the study examples mentioned below, 2-[2-(1-hydroxycyclohexyl)-1-ethyn-1-yl]-$N^9$-propargyladenine described in Patent Literature 2, and a compound represented by the following formula:

[Formula 2]

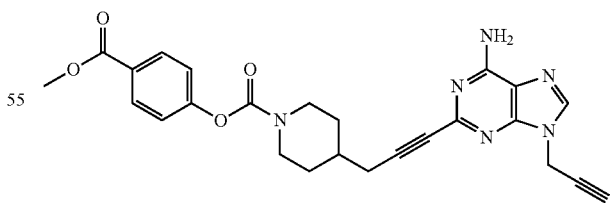

which is listed as a representative compound in Patent Literature 3, compound No. 9 in [Table A], have no potent activity as a potent adenosine $A_{2a}$ receptor antagonist, and they cannot necessarily be said to be a promising compound.

Patent Literature 4 also discloses an adenosine $A_{2a}$ receptor antagonist having adenine as a basic skeleton; however, it does not disclose the compound of the present invention as a specific compound, including the synthesis method thereof. In addition, Patent Literature 4 only discloses the use as a prophylactic or therapeutic agent for diabetes and diabetic complications, which has no relation to the use of the compound of the present invention.

Accordingly, it has been desired to develop a novel selective adenosine $A_{2a}$ receptor antagonist the effect of which, as a therapeutic agent for Parkinson's syndrome, is stronger and more continuous.

Solution to Problem

Conventionally a large number of adenosine $A_{2a}$ receptor antagonists having adenine as a basic skeleton have been known, and Patent Literatures 2 to 4 also describe many compounds having different substituents or structures. However, for the above compounds, it has not previously fully been pursued to clarify, among numerous structures such as substituents, what factors are entailed in a compound which has a more potent adenosine $A_{2a}$ receptor antagonist activity or which exhibits a strong effect on improvement of Parkinson's syndrome. Furthermore, as for compounds having substituents and structures like the compound of the present invention, their chemical structures, antagonist activities, and the intensity of improving effect on Parkinson's syndrome have never been known.

Accordingly, the present inventors have diligently worked on studies to newly find that a 2-alkynyl-$N^9$-propargyladenine represented by the following formula (I) unexpectedly has an adenosine $A_{2a}$ receptor antagonist activity more potent than conventional compounds and improves various symptoms of movement disorder accompanied by Parkinson's syndrome remarkably compared with conventional compounds, and also that administration of the formula (I) compound to a patient with Parkinson's syndrome, singly or in combination with another drug, can be expected to be able to improve the symptoms of Parkinson's syndrome with a smaller dose, for a long time period, and accordingly can solve the problems with conventional therapeutic agents for Parkinson's syndrome as an adenosine $A_{2a}$ receptor antagonist, thereby completing the present invention.

That is, the present invention relates to the following (1) to (19):

(1) A 2-alkynyl-$N^9$-propargyladenine represented by the following formula (I):

[Formula 3]

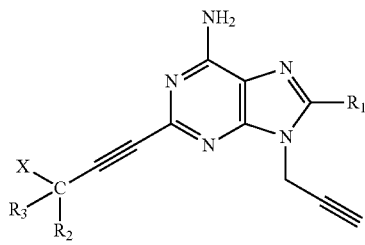

(I)

wherein $R_1$ represents halogen, a furyl group or a triazolyl group; $R_2$ and $R_3$ each represent hydrogen or an alkyl group having 1 to 8 carbon atoms, or $R_2$ and $R_3$ represent a cycloalkyl group in which $R_2$ and $R_3$ are linked together; and X represents hydrogen or a hydroxyl group, or a pharmaceutically acceptable salt thereof.

(2) The 2-alkynyl-$N^9$-propargyladenine or a pharmaceutically acceptable salt thereof according to (1), wherein $R_1$ is bromo or chloro.

(3) The 2-alkynyl-$N^9$-propargyladenine or a pharmaceutically acceptable salt thereof according to (1), wherein $R_1$ is a 2-furyl group or a 2-triazolyl group.

(4) The 2-alkynyl-$N^9$-propargyladenine or a pharmaceutically acceptable salt thereof according to (1), wherein $R_2$ is hydrogen and $R_3$ is an alkyl group having 1 to 8 carbon atoms.

(5) The 2-alkynyl-$N^9$-propargyladenine or a pharmaceutically acceptable salt thereof according to (1), wherein $R_2$ and $R_3$ are a cycloalkyl group in which $R_2$ and $R_3$ are linked together.

(6) The 2-alkynyl-$N^9$-propargyladenine or a pharmaceutically acceptable salt thereof according to (1), which is 8-bromo-2-alkynyl-$N^9$-propargyladenine, or 8-chloro-2-alkynyl-N9-propargyladenine.

(7) The 2-alkynyl-$N^9$-propargyladenine or a pharmaceutically acceptable salt thereof according to (1), which is 8-(2-furyl)-2-alkynyl-$N^9$-propargyladenine, or 8-(1,2,3-triazol-2-yl)-2-(1-alkynyl)-$N^9$-propargyladenine.

(8) The 2-alkynyl-$N^9$-propargyladenine or a pharmaceutically acceptable salt thereof according to (1), which is 8-bromo-2-(1-hydroxycycloalkyl)ethynyl-$N^9$-propargyladenine, or 8-chloro-2-(1-hydroxycycloalkyl)ethynyl-$N^9$-propargyladenine.

(9) The 2-alkynyl-$N^9$-propargyladenine or a pharmaceutically acceptable salt thereof according to (1), which is 8-(2-furyl)-2-(1-hydroxycycloalkyl)ethynyl-$N^9$-propargyladenine, or 8-(1,2,3-triazol-2-yl)-2-(1-hydroxycycloalkyl)ethynyl-$N^9$-propargyladenine.

(10) A pharmaceutical composition comprising the 2-alkynyl-$N^9$-propargyladenine or a pharmaceutically acceptable salt thereof according to any one of (1) to (9), and a pharmaceutically acceptable carrier.

(11) The pharmaceutical composition according to (10) for use as an adenosine $A_{2a}$ receptor antagonist.

(12) The pharmaceutical composition according to (10) or (11) for use in the treatment of Parkinson's syndrome.

(13) The pharmaceutical composition according to any one of (10) to (12), for use in combination with another adenosine $A_{2a}$ receptor antagonist or another therapeutic agent for Parkinson's syndrome.

(14) The pharmaceutical composition according to any one of (10) to (13), for use in combination with one or more therapeutic agents for Parkinson's syndrome selected from the group consisting of L-DOPA, dopamine, dopaminergic agonists, monoamine oxidase B inhibitors (MAO-B), DOPA decarboxylase inhibitors (DCI), or catechol-O-methyltransferase (COMT) inhibitors.

(15) A kit comprising the 2-alkynyl-$N^9$-propargyladenine or a pharmaceutically acceptable salt thereof according to any one of (1) to (9), and another adenosine $A_{2a}$ receptor antagonist or another therapeutic agent for Parkinson's syndrome.

(16) A kit for the treatment of Parkinson's syndrome, comprising the 2-alkynyl-$N^9$-propargyladenine or a pharmaceutically acceptable salt thereof according to any one of (1) to (9), and one or more therapeutic agents for Parkinson's syndrome selected from the group consisting of L-DOPA, dopamine, dopaminergic agonists, monoamine oxidase B inhibitors (MAO-B), DOPA decarboxylase inhibitors (DCI), or catechol-O-methyltransferase (COMT) inhibitors.

(17) A method for treating Parkinson's syndrome, comprising administering to a subject in need thereof the 2-alkynyl-$N^9$-propargyladenine or a pharmaceutically acceptable salt thereof according to any one of (1) to (9).

(18) A method for treating Parkinson's syndrome, comprising administering to a subject in need thereof, simultaneously or separately, the 2-alkynyl-$N^9$-propargyladenine or a pharmaceutically acceptable salt thereof according to any one of (1) to (9), and another adenosine $A_{2a}$ receptor antagonist or another therapeutic agent for Parkinson's syndrome.

(19) A method for treating Parkinson's syndrome, comprising administering to a subject in need thereof, simultaneously or separately, the 2-alkynyl-$N^9$-propargyladenine or a pharmaceutically acceptable salt thereof according to any one of (1) to (9), and one or more therapeutic agents for Parkinson's syndrome selected from the group consisting of L-DOPA, dopamine, dopaminergic agonists, monoamine oxidase B inhibitors (MAO-B), DOPA decarboxylase inhibitors (DCI), or catechol-O-methyltransferase (COMT) inhibitors.

Advantageous Effects of Invention

The compound of the present invention has high chemical stability, especially high photostability, exerts the effect with a smaller dose, in addition, over a long period of time, as compared with previously reported therapeutic agents for Parkinson's syndrome as an adenosine $A_{2a}$ receptor antagonist, and is extremely useful as a therapeutic agent for Parkinson's syndrome. Moreover, the combination of the compound of the present invention with L-DOPA, the efficacy of which has conventionally been known to be lowered by long-term administration, can be expected to provide a stronger improving effect on symptoms, and moreover, can control the lowering of the efficacy of L-DOPA by long-term use.

Figure 1:
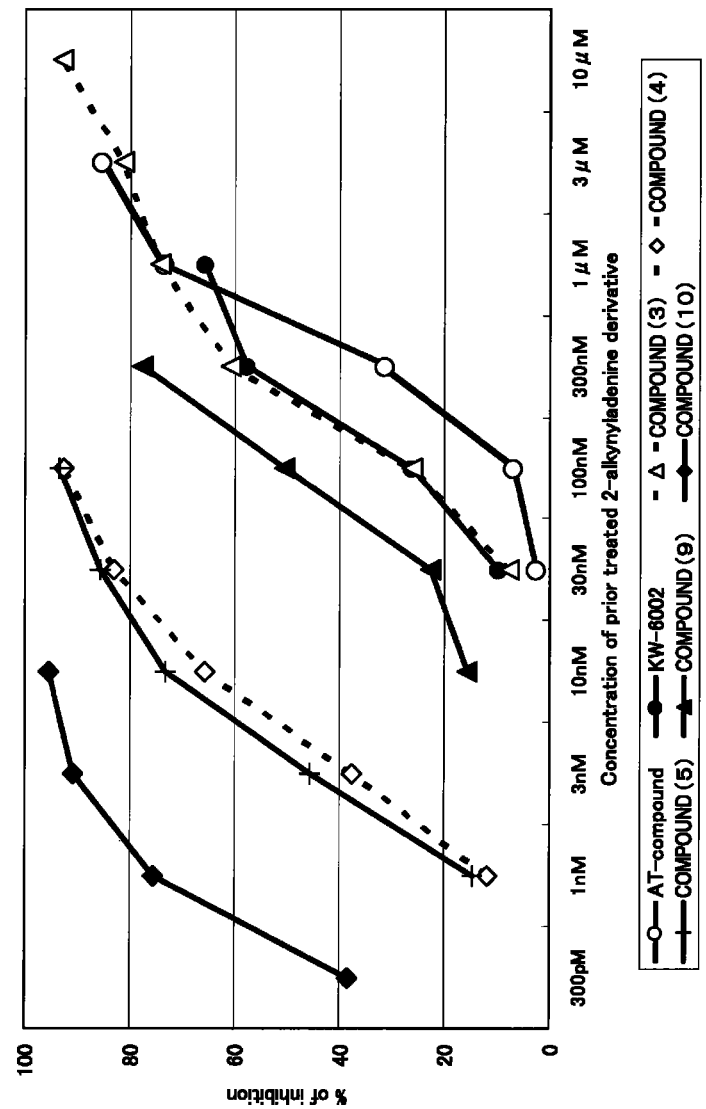
FIG. 1 shows the results of the determination of the adenosine $A_{2a}$ receptor antagonist activity of the compound of the present invention, determined by using the Magnus method. The vertical line represents the intensity of the inhibition of the relaxing response of the femoral vein when each substance was added in an organ bath, and the horizontal line represents the concentration of each substance added.

DESCRIPTION OF EMBODIMENTS (1) Compound of the Present Invention

The compound of the present invention is a 2-alkynyl-$N^9$-propargyladenine represented by the following formula (I):

[Formula 4]

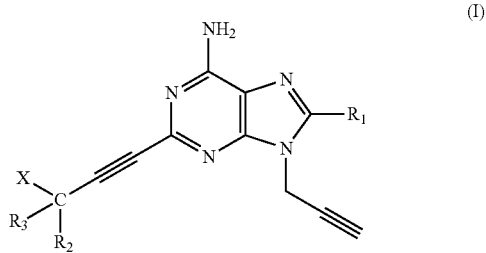

or a pharmaceutically acceptable salt thereof, wherein $R_1$ represents halogen, a furyl group or a triazolyl group; $R_2$ and $R_3$ each represent hydrogen or an alkyl group having 1 to 8 carbon atoms, or $R_2$ and $R_3$ represent a cycloalkyl group in which $R_2$ and $R_3$ are linked together; and X represents hydrogen or a hydroxyl group.

In the formula, $R_1$ represents halogen, a furyl group or a triazolyl group. Examples of halogen can include chloro, bromo, or iodo, and examples of furyl groups can include 2-furyl or 3-furyl. Examples of triazolyl groups can include 1-triazolyl or 2-triazolyl.

$R_2$ and $R_3$ each represent hydrogen or an alkyl group having 1 to 8 carbon atoms, or $R_2$ and $R_3$ represent a cycloalkyl group in which $R_2$ and $R_3$ are linked together. The alkyl group having 1 to 8 carbon atoms is a straight or branched chain alkyl group having 1 to 8 carbon atoms, and specifically, examples of the alkyl group can include methyl, ethyl, propyl, isopropyl, butyl, isobutyl, secondary butyl, tertiary butyl, pentyl, isopentyl, neopentyl, hexyl, isohexyl, heptyl, or octyl. The cycloalkyl group in which $R_2$ and $R_3$ are linked together is a cyclic alkyl group having 3 to 10 carbon atoms, and specifically, examples of such cycloalkyl group can include cyclopropyl, cyclobutyl, cyclopentyl, cyclohexyl, or adamantyl.

Of the compounds of the present invention, a preferred compound is one which satisfies one or more of the following conditions:

(a) $R_1$ is bromo or chloro;
(b) $R_1$ is 2-furyl or 2-triazolyl;
(c) $R_2$ is hydrogen and $R_3$ is an alkyl group having 1 to 8 carbon atoms; and (d) $R_2$ and $R_3$ are a cycloalkyl group in which $R_2$ and $R_3$ are linked together.

Examples of a more preferred compound can include a compound which satisfies the above (a) and (c), a compound which satisfies (a) and (d), a compound which satisfies (b) and (c), or a compound which satisfies (b) and (d).

Specifically, examples of such preferred compound can include 8-bromo-2-alkynyl-$N^9$-propargyladenine, such as 8-bromo-2-(1-octyn-1-yl)-$N^9$-propargyladenine, which satisfies the above (a) and (c), and in which X is hydrogen;

8-chloro-2-alkynyl-$N^9$-propargyladenine, such as 8-chloro-2-(1-octyn-1-yl)-$N^9$-propargyladenine, which also satisfies the above (a) and (c), and in which X is hydrogen;

8-bromo-2-[2-(1-hydroxycycloalkyl)-1-ethyn-1-yl]-$N^9$-propargyladenine, such as 8-bromo-2-[2-(1-hydroxycyclohexyl)-1-ethyn-1-yl]-$N^9$-propargyladenine, which satisfies the above (a) and (d), and in which X is a hydroxyl group;

8-chloro-2-[2-(1-hydroxycycloalkyl)-1-ethyn-1-yl]-$N^9$-propargyladenine, such as 8-chloro-2-[2-(1-hydroxycyclohexyl)-1-ethyn-1-yl]-$N^9$-propargyladenine, which also satisfies the above (a) and (d), and in which X is a hydroxyl group;

8-(2-furyl)-2-alkynyl-$N^9$-propargyladenine, such as 8-(2-furyl)-2-(1-octyn-1-yl)-$N^9$-propargyl-adenine, which satisfies the above (b) and (c), and in which X is hydrogen;

8-(2-triazolyl)-2-alkynyl-$N^9$-propargyladenine, such as 8-(2-triazolyl)-2-(1-octyn-1-yl)-$N^9$-propargyl-adenine, which also satisfies the above (b) and (c), and in which X is hydrogen; or 8-(2-furyl)-2-(1-hydroxycycloalkyl)ethynyl-$N^9$-propargyladenine, such as 8-(2-furyl)-2-[2-(1-hydroxycyclohexyl)-1-ethyn-1-yl]-$N^9$-propargyladenine, which satisfies the above (b) and (d), and in which X is a hydroxyl group.

The compound of the present invention may be in the form of a pharmaceutically acceptable salt, or in the form of a hydrate or a solvate. Examples of such salts include any pharmaceutically acceptable salts such as hydrochloride, sulfate, or phosphate, or organic acid salts such as citric acid.

Examples of the hydrates or solvates can include one in which 0.1 to 3.0 molecules of water or a solvent are attached to 1 molecule of the compound of the present invention or a salt thereof. In addition, various types of isomers such as tautomers can also be included in the compound of the present invention.

(2) Production Method of the Compound of the Present Invention

The compound of the present invention can be synthesized, for example, via two steps described below.

[Formula 5]

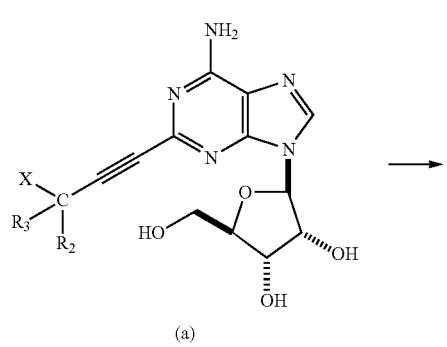

(a)

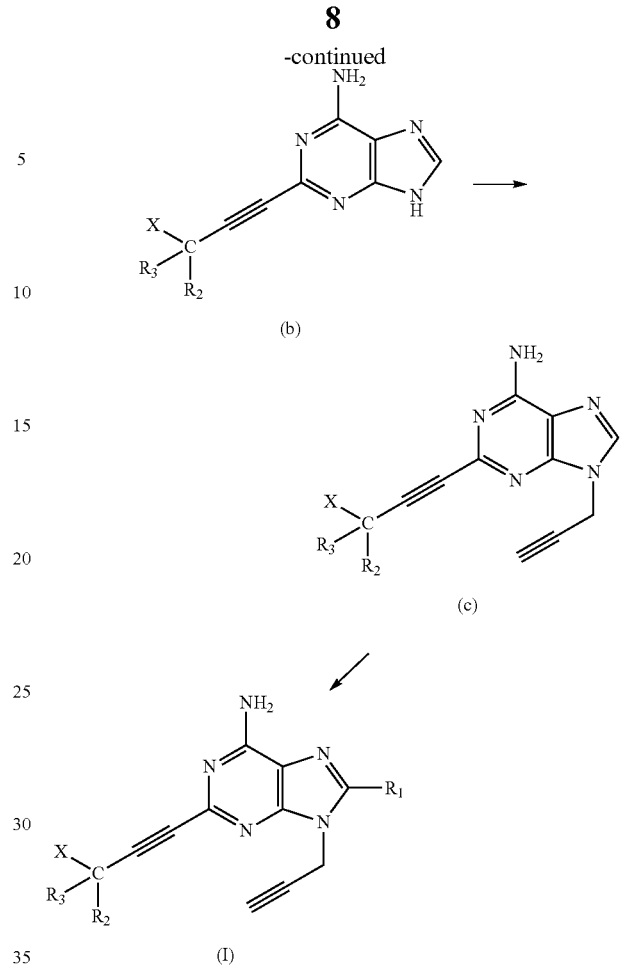

In the formula, $R_1$ to $R_3$ and X mean the same as those aforementioned.

Step 1

Step 1 is a step of deribosylating a 2-alkynyladenosine derivative (formula a compound), which is used as a raw material compound, by a hydrolysis reaction to obtain a 2-alkynyladenine derivative (formula b compound).

The raw material compound, formula a compound can be prepared based on the method of a publicly-known literature (J. Med. Chem., 1992, 35, 2253) or the like.

The hydrolysis reaction can be performed by incubation in an aqueous solvent such as water or dioxane, using an acid such as hydrochloric acid or sulfuric acid, under acidic condition, at 50 to 120° C. for approximately 1 to 10 hours.

Step 2

Step 2 is a step of treating the above 2-alkynyladenine derivative (formula b compound) with a propargyl halide such as propargyl bromide to synthesize a 2-alkynyl-$N^9$-propargyladenine derivative (formula c compound) having a propargyl group at position $N^9$, and then performing halogenation at position 8 to obtain the compound of the present invention.

The reaction of the formula b compound with a propargyl halide can be performed by carrying out the reaction in a single or mixed solvent such as dimethylformamide or dimethylsulfoxide, in the presence of a base such as potassium carbonate or sodium carbonate, using 1 to 3 moles of the propargyl halide with respect to 1 mole of the formula b compound, at 10 to 50° C. for approximately 1 to 10 hours.

The halogenation reaction at position 8 in the formula c compound can be performed by carrying out the reaction using a halogenating agent such as chlorine, bromine, iodine, or N-halogenosuccinimides such as N-bromosuccinimide, in a single or mixed solvent such as dimethylformamide or dimethylsulfoxide, in the presence of a base such as potassium acetate, using approximately 1 to 3 moles of the halogenating agent with respect to 1 mole of the formula c compound, at 10 to 50° C. for approximately 1 to 10 hours.

The furylation reaction at position 8 in the formula c compound can be performed by carrying out the reaction using 1 to 3 moles of a furylboronic acid derivative such as 2-furylboronic acid as a furylating agent with respect to 1 mole of the compound which has been subjected to the above halogenation at position 8, in the presence of a palladium catalyst and a base such as potassium carbonate, at 80° C. for approximately 1 to 10 hours.

The compound of the present invention thus obtained can be isolated and purified by appropriately combining methods routinely used for isolation and purification of nucleobases (for example, various types of chromatography such as adsorption or ion exchange chromatography, recrystallization methods, or the like).

(3) Pharmaceutical Use of the Compound of the Present Invention

As shown in the Examples mentioned below, the compound of the present invention exerts an effect with a smaller dose, in addition, for a long time, as compared with previously reported adenosine $A_{2a}$ receptor antagonists as a therapeutic agent for Parkinson's syndrome, and is extremely promising as an adenosine $A_{2a}$ receptor antagonist, especially as a therapeutic agent for Parkinson's syndrome.

In addition, the combination of the compound of the present invention with L-DOPA, the efficacy of which has conventionally been known to be lowered by long-term administration, can be expected to provide a stronger improving effect on symptoms, and moreover, can be expected to control the lowering of the efficacy of L-DOPA by long-term use.

The compound of the present invention may be administered singly or in combination with one or more of other drugs used for the treatment of Parkinson's syndrome. The other drug used for the treatment of Parkinson's syndrome may be selected from those usually used. For example, such drugs can include L-DOPA, dopamine, dopaminergic agonists, monoamine oxidase B inhibitors (MAO-B), DOPA decarboxylase inhibitors (DCI), or catechol-O-methyltransferase (COMT) inhibitors.

The compound of the present invention can be administered as a pharmaceutical product, a supplement, an enteral nutrient, health food and beverages, or the like. In addition, upon administration, the compound of the present invention can be used as an active ingredient, in combination with pharmaceutical aids (such as diluents, binders, disintegrants, lubricants, flavoring agents, solubilizing aids, suspending agents, coatings), and made into various types of compositions such as tablets, capsules, granules, powders, syrups, injections, suppositories, creams, aerosols, or the like according to conventional methods.

In addition, the compound of the present invention may be made into a kit, together with another adenosine $A_{2a}$ receptor antagonist, particularly one or more of other drugs used for the treatment of Parkinson's syndrome.

The administration or intake method is not particularly limited; however, oral administration is preferable. The dose or intake amount may be about 1 to 2000 mg/day, preferably about 10 to 1000 mg/day, although it varies depending on the age, body weight, and severity of symptoms of the subject, administration or intake method, or the like. In addition, in the case of administration in combination with another drug used for the treatment of Parkinson's syndrome such as L-DOPA, the doses of both drugs, the compound of the present invention and L-DOPA, may be about 1 to 2000 mg/day and approximately 10 to 1000 mg/day, respectively.

Additionally, the compound of the present invention may be mixed with a biodegradable sustained-release carrier and administered in the form of an implant. In addition, for the purpose of sustained-release of the active ingredient, the preparation can be formulated such that the active ingredient is made into a transdermal patch. For the production method of implants and transdermal patches, a well known method may be used.

EXAMPLES

Hereinafter, the present invention will be described specifically by referring to the Examples; however, the present invention is clearly not limited to these Examples.

Example 1

Synthesis of the Compound of the Present Invention (A) Synthesis of the Formula (4) Compound and the Formula (5) Compound As a compound of the present invention, 8-bromo-2-(1-octyn-1-yl)-$N^9$-propargyladenine (formula (I): $R_1$=Br, $R_2$=H, $R_3$=$C_6H_{13}$, X=H) (formula (4) compound)), and 8-(2-furyl)-2-(1-octyn-1-yl)-$N^9$-propargyl-adenine ($R_1$=H, $R_2$=2-furyl, $R_3$=$C_6H_{13}$, X=H) (formula (5) compound)) were synthesized according to the synthetic route represented by the following scheme.

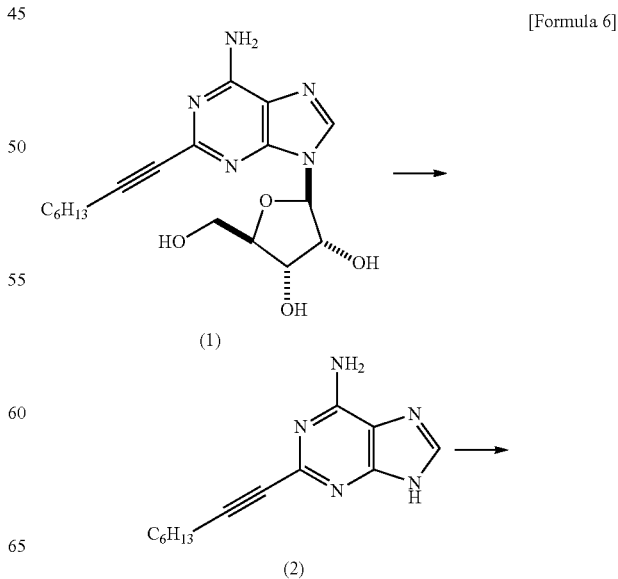

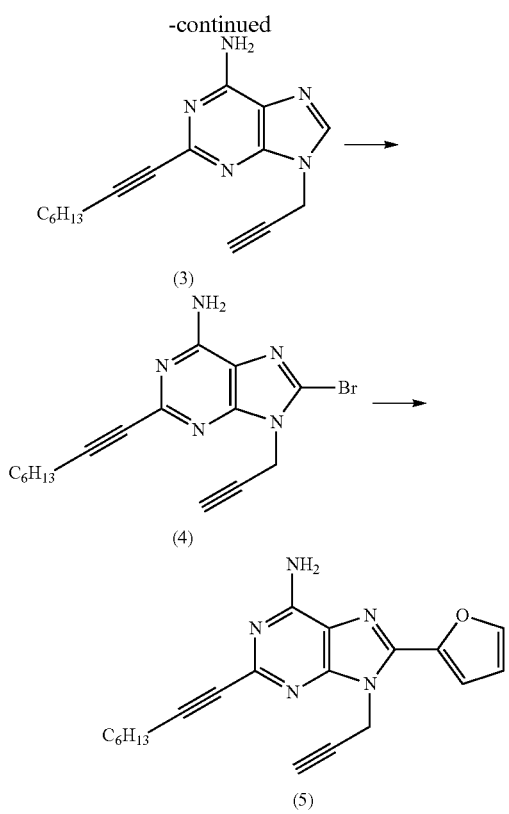

Step 1

Synthesis of the formula (2) compound: 2-(1-octyn-1-yl)adenine

The formula (1) compound: 2-(1-octyn-1-yl)adenosine, which is a raw material compound, was synthesized according to the method of a reference literature (J. Med. Chem., 1992, 35, 2253). Then, 3.0 g (8.0 mmol) of 2-(1-octyn-1-yl) adenosine was added to 30 mL of dioxane, and 30 mL of 0.6 M HCl was further added thereto, and the mixture was stirred at 100° C. for 6 hours. After neutralization with 0.6 M NaOH, the precipitated crystals were collected by filtration and washed with methanol to give 1.79 g (92%) of the formula (2) compound: 2-(1-octyn-1-yl)adenine.

1H-NMR (DMSO-$d_6$): δ 12.85 (1H, brs), 8.11 (1H, s), 7.20 (2H, s), 2.39 (2H, t, J=7.0 Hz), 1.56-1.27 (8H, m), 0.88 (3H, t, J=6.8 Hz)

Step 2-1

Synthesis of the formula (4) compound: 8-bromo-2-(1-octyn-1-yl)-$N^9$-propargyladenine To a solution of 0.2 g (0.82 mmol) of the formula (2) compound synthesized: 2-(1-octyn-1-yl)adenine and 0.23 g (1.64 mmol) of potassium carbonate in 5 mL of DMF was added 0.12 mL (1.64 mmol) of propargyl bromide, and the mixture was stirred at room temperature for 6.5 hours. To the reaction solution was added water, and the mixture was extracted with ethyl acetate, and the extract was dried over anhydrous magnesium sulfate. The solvent was distilled off, and the residue was purified by silica gel column chromatography (hexane/ethyl acetate=1/7) to give 177 mg (77%) of the formula (3) compound of interest.

1H-NMR(CDCl$_3$): δ 8.04 (1H, s) 5.83 (2H, brs), 4.98 (2H, d, J=2.6 Hz), 2.53 (1H, t, J=2.5 Hz), 2.45 (2H, t, J=7.4 Hz), 1.69-1.63 (2H, m), 1.48-1.35 (2H, m), 1.34-1.24 (4H, m), 0.89 (3H, t, J=6.8 Hz)

To a solution of 0.5 g (1.78 mmol) of the formula (3) compound obtained: 2-(1-octyn-1-yl)-$N^9$-propargyladenine and 39 mg (0.4 mmol) of potassium acetate in 5 mL of DMF was added 0.47 g (2.66 mmol) of N-bromosuccinimide, and the mixture was stirred at room temperature for 1 hour. To the reaction solution was added water, and the mixture was extracted with ethyl acetate, and the extract was dried over anhydrous magnesium sulfate. The solvent was distilled off, and the residue was purified by silica gel column chromatography (hexane/ethyl acetate=1/1) to give 334 mg (52%) of the formula (4) compound of interest.

1H-NMR (DMSO-$d_6$): δ 7.56 (2H, brs), 4.93 (2H, d, J=2.3 Hz), 3.47 (1H, t, J=2.4 Hz), 2.41 (2H, t, J=9.4 Hz), 1.57-1.51 (2H, m), 1.43-1.33 (2H, m), 1.32-1.27 (4H, m), 0.88 (3H, t, J=6.8 Hz)

Step 2-2

Synthesis of the formula (5) compound: 8-(2-furyl)-2-(1-octyn-1-yl)-$N^9$-propargyl-adenine A solution of 50 mg (0.14 mmol) of the above formula (4) compound: 8-bromo-2-(1-octyn-1-yl)-$N^9$-propargyladenine, and 31 mg (0.28 mmol) of 2-furylboronic acid, 38 mg (0.27 mmol) of potassium carbonate, and 32 mg (0.028 mmol) of tetrakis triphenylphosphine palladium in 2 mL of water/3 mL of dioxane was stirred under argon atmosphere at 80° C. for 30 minutes, and then another 16 mg (0.014 mmol) of tetrakis triphenylphosphine palladium was added thereto, and the mixture was stirred for additional 1 hour. To the reaction solution was added water, and the mixture was extracted with ethyl acetate, and the extract was dried over anhydrous magnesium sulfate. The solvent was distilled off, and the residue was purified by silica gel column chromatography (hexane/ethyl acetate=3/2) to give 20 mg (41%) of the formula (5) compound of interest.

1H-NMR (DMSO-$d_6$): δ 8.02 (1H, s), 7.52 (2H, brs), 7.25 (1H, d, J=3.4 Hz), 6.79 (1H, dd, J=1.1&2.8 Hz), 5.18 (2H, d, J=1.8 Hz), 3.40 (1H, s), 2.42 (2H, t, J=7.0 Hz), 1.58-1.52 (2H, m), 1.43-1.39 (2H, m), 1.31-1.30 (4H, m), 0.88 (3H, t, J=6.5 Hz)

(B) Synthesis of the Formula (10) Compound

Furthermore, starting from the formula (6) compound, via the formula (9) compound, for the formula (10) compound of the present invention, 8-bromo-2-[2-(1-hydroxycyclohexyl)-1-ethyn-1-yl]-$N^9$-propargyladenine (formula (I): $R_1$=Br, $R_2$=$R_3$=$C_6H_{11}$, X=OH) (formula (10) compound)) was synthesized according to the synthetic route shown in the following scheme.

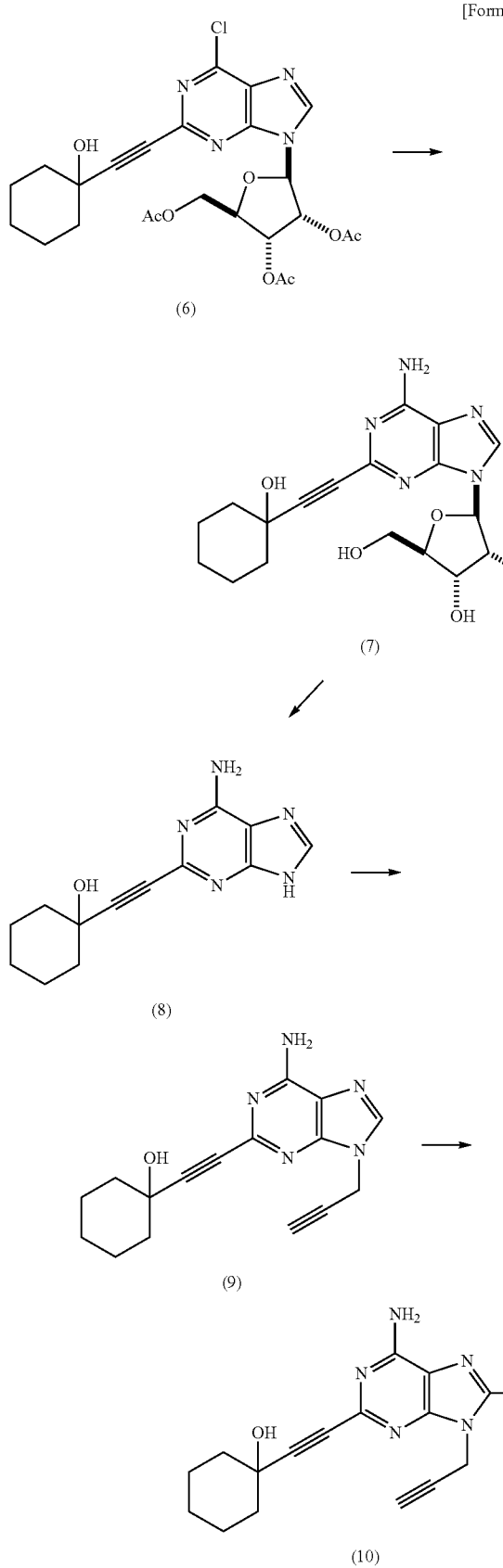

[Formula 7]

Step 1

The formula (6) compound: 6-chloro-2-[2-(1-hydroxycyclohexyl)-1-ethyn-1-yl]-9-(2,3,5-tri-O-acetyl-β-D-ribofuranosyl)purine, which is a raw material compound, was synthesized according to the method of a reference document (J. Med. Chem., 1992, 35, 2253), and to a solution of 1.38 g (2.58 mmol) of this compound in 16 mL of dioxane was added 8 mL of 28% ammonia water, and the mixture was stirred in a sealed tube at 70° C. for 22 hours. The reaction solution was concentrated, and then ethanol was added thereto to perform azeotroping. The residue was crudely purified by silica gel column chromatography (hexane/ethyl acetate=6/1) to give the formula (7) compound: 2-[2-(1-hydroxycyclohexyl)-1-ethyn-1-yl]adenosine. To this compound was added 10 mL of dioxane and 10 mL of 0.6 M hydrochloric acid, and the mixture was stirred at 100° C. for 5.5 hours. After cooling, the reaction solution was neutralized with a 0.4 M sodium hydroxide aqueous solution, and after concentration of this solution, the precipitated crystals were collected by filtration, and washed with water and methanol to give 263 mg (39%) of the formula (8) compound: 2-[2-(1-hydroxycyclohexyl)-1-ethyn-1-yl]adenine.

1H-NMR (DMSO-$d_6$): δ 13.19-12.39 (1H, br), 8.13 (1H, brs), 7.23 (2H, brs), 5.49 (1H, s), 1.91-1.24 (10H, m)

Step 2

Then, to a solution of 261 mg (1.01 mmol) of the formula (8) compound synthesized: 2-[2-(1-hydroxycyclohexyl)-1-ethyn-1-yl]adenine and 280 mg (2.02 mmol) of potassium carbonate in 30 mL of DMF was added 0.15 mL (2.02 mmol) of propargyl bromide, and the mixture was stirred for 3 hours. The reaction solution was concentrated, the crystals were filtered off, and the filtrate was concentrated. The residue was purified by silica gel column chromatography (chloroform/methanol=9/1) to give 208 mg (69%) of the formula (9) compound of interest.

1H-NMR (DMSO-$d_6$): δ 8.23 (1H, s), 7.43 (2H, brs), 5.54 (1H, s), 5.02 (2H, d, J=2.4 Hz), 3.48 (1H, t, J=2.1 Hz), 1.85-1.29 (10H, m)

To a solution of 0.16 g (0.54 mmol) of the formula (9) compound obtained: 2-[2-(1-hydroxycyclohexyl)-1-ethyn-1-yl]-$N^9$-propargyladenine in 5 mL of DMF was added 0.1 g (0.56 mmol) of N-bromosuccinimide, and the mixture was stirred for 1.5 hours. To the solution was added 1 mg (0.01 mmol) of potassium acetate, and the mixture was stirred for 2.5 hours, and then 3 mg (0.03 mmol) of potassium acetate was further added thereto, and the mixture was stirred for 2 hours. Subsequently, to the reaction solution was added 100 mg (0.56 mmol) of N-bromosuccinimide, and the mixture was stirred for 2 hours. To the reaction solution was added water, and the mixture was extracted with ethyl acetate, and the organic layer was washed with a saturated saline solution and dried over anhydrous magnesium sulfate. The solvent was distilled off, and the residue was purified by silica gel column chromatography (ethyl acetate only) to give 60 mg (30%) of the formula (10) compound of interest.

1H-NMR (DMSO-$d_6$): δ 7.63 (2H, brs), 5.59 (1H, s), 4.95 (2H, d, J=2.1 Hz), 3.49 (1H, t, J=2.3 Hz), 1.85-1.26 (10H, m)

(C) Synthesis of the Formula (11) Compound, the Formula (12) Compound, the Formula (13) Compound, and the Formula (14) Compound In addition, synthesis of compounds of formulae (11) to (15) was also performed as follows.

[Formula 8]

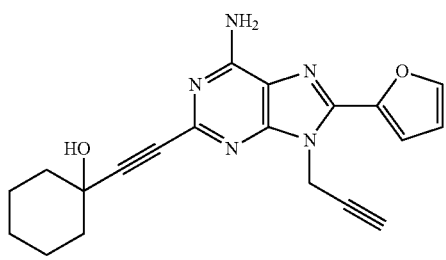

(11)

(12)

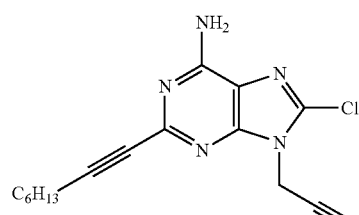

(13)

(14)

Synthesis of the formula (11) compound: 8-(2-furyl)-2-[2-(1-hydroxycyclohexyl)-1-ethyn-1-yl]-$N^9$-propargyladenine The formula (10) compound synthesized by the aforementioned method: 8-bromo-2-[2-(1-hydroxycyclohexyl)-1-ethyn-1-yl]-$N^9$-propargyladenine (1.0 g, 2.7 mmol), and 2-furylboronic acid (598 mg, 5.3 mmol), tetrakis triphenylphosphine palladium (309 mg, 0.27 mmol), and potassium carbonate (738 mg, 5.3 mmol) were dissolved in dioxane (30 mL) and water (20 mL), and the mixture was stirred at 100° C. for 25 minutes. Chloroform and water were added thereto to perform partitioning, and the organic layer was dried over anhydrous sodium sulfate. After filtration, the filtrate was concentrated under reduced pressure, and the residue was purified by silica gel column chromatography (0 to 3% methanol-chloroform). The obtained compound was suspended in chloroform, and the solid was collected by filtration to give the formula (11) compound (155 mg, 0.43 mmol, 16%).

1H-NMR (DMSO-$d_6$): δ 8.03 (1H, d, J=1.7 Hz), 7.60 (2H, brs), 7.27 (1H, d, J=3.4 Hz), 6.80 (1H, dd, J=1.7 Hz, 3.4 Hz), 5.58 (1H, s), 5.21 (2H, d, J=2.4 Hz), 3.42 (1H, t, J=2.4 Hz), 1.86-1.23 (10H, m)

ESI-MS: 362 (M+H)+

Synthesis of the formula (12) compound: 8-chloro-2-(1-octynyl)-$N^9$-propargyladenine The formula (2) compound: 2-(1-octynyl)-$N^9$-propargyladenine (281 mg, 1.00 mmol) was dissolved in dimethylformamide (10 mL), and N-chlorosuccinimide (267 mg, 2.0 mmol) and potassium acetate (29 mg, 0.30 mmol) was added thereto, and the mixture was stirred for 30 hours. A saturated sodium thiosulfate aqueous solution was added thereto to stop the reaction, and then the mixture was extracted with ethyl acetate, and the organic layer was dried over anhydrous magnesium sulfate. After filtration, the filtrate was concentrated under reduced pressure, and the residue was dissolved in chloroform and purified by silica gel column chromatography (hexane:ethyl acetate 3:1). The formula (12) compound was obtained (173 mg, 55%).

1H-NMR(CDCl$_3$): 5.58 (2H, brs), 4.98 (2H, d, J=2.5 Hz), 2.46 (2H, t, J=7.3 Hz), 2.36 (1H, t, J=2.5 Hz), 1.69-1.25 (8H, m), 0.89 (3H, t, J=6.5 Hz)

ESI-MS: 316 (M+H)+

Synthesis of the formula (13) compound: 8-chloro-2-[2-(1-hydroxycyclohexyl)-1-ethyn-1-yl]-$N^9$-propargyladenine The formula (9) compound: 2-[2-(1-hydroxycyclohexyl)-1-ethyn-1-yl]-$N^9$-propargyladenine (200 mg, 0.67 mmol) was dissolved in dimethylformamide (7 mL), and N-chlorosuccinimide (180 mg, 1.3 mmol) and potassium acetate (20 mg, 0.20 mmol) was added thereto, and the mixture was stirred for 28.5 hours. A saturated sodium thiosulfate aqueous solution was added thereto to stop the reaction, and then the mixture was extracted with chloroform, and the organic layer was dried over anhydrous sodium sulfate. After filtration, the filtrate was concentrated under reduced pressure, the residue was suspended in chloroform, and the solid was collected by filtration to give the product of interest (49 mg, 0.15 mmol, 22%).

1H-NMR (DMSO-$d_6$): 7.60 (2H, brs), 5.55 (1H, s), 4.98 (2H, d, J=2.3 Hz), 3.48 (1H, t, J=2.3 Hz), 1.85-1.25 (10H, m)

ESI-MS: 352 (M+Na)+

Synthesis of the formula (14) compound: 8-(1,2,3-triazol-2-yl)-2-(1-octynyl)-$N^9$-propargyladenine The formula (4) compound: 8-bromo-2-octynyl-$N^9$-propargyladenine (500 mg, 1.4 mmol), 1,2,3-triazole (96 mg, 1.4 mmol), and potassium carbonate (192 mg, 1.4 mmol) was dissolved in DMF (5 mL), and the mixture was stirred at 100° C. for 1 hour. Chloroform and water was added thereto to perform partitioning, and the organic layer was dried over anhydrous magnesium sulfate. After filtration, the filtrate was concentrated under reduced pressure, and the residue was purified by silica gel column chromatography (hexane: ethyl acetate 3:1→1:1). The crude purified product obtained was re-purified by ODS column chromatography (acetonitrile-water 20%→50%) to give the formula (14) compound: 1,2,3-triazol-2-yl body (20 mg, 4%).

1H-NMR(CDCl$_3$): 8.03 (2H, s), 6.33 (2H, brs), 5.47 (2H, d, J=2.4 Hz), 2.48 (2H, t, J=7.4 Hz), 2.16 (1H, t, J=2.5 Hz), 1.69-1.30 (8H, m), 0.90 (3H, t, J=3.4 Hz)

ESI-MS: 349 (M+H)+

Example 2

Evaluation of the Adenosine $A_{2a}$ Receptor for Antagonist Activity of the Compound of the Present Invention by the Magnus Method Evaluation Method:

In order to clarify the adenosine $A_{2a}$ receptor antagonist activity of the compound of the present invention, an evaluation by the Magnus method was conducted. The Magnus method is a method of evaluating the action of drugs using muscle contraction/relaxation as an index, and is used generally as a method for determining the antagonist activity.

In the evaluation, firstly, the femoral vein was excised from male Wistar rats. A Krebs-Henseleit solution aerated with $O_2$ gas was filled in an organ bath and kept at 37° C., and the excised femoral vein was suspended therein under 0.5 g of resting tension. The contractile and relaxing response was determined via a pickup transducer.

In order to check the reactivity of the compound, firstly, the test compound was added dropwise in the organ bath. 10 minutes after the dropwise addition, serotonin was added dropwise in the organ bath such that the concentration thereof was $10^{-5}$ M, to make the femoral vein contract. In a state where the contractile response was stable, $10^{-7}$ M of an adenosine $A_{2a}$ receptor agonist, 2-octynyladenosine was administered to induce the relaxing response, and the inhibitory effect of the compound of the present invention and a positive control on the relaxing response was evaluated. Note that, in the representation of the results, the degree of the contraction at the time of addition of each substance was calculated, on condition that the degree of the relaxation when the compound of the present invention and the positive control were not added dropwise at all was designated as a control for the whole, and the degree of the relaxation for the control for the whole was set to be 100%.

As a compound of the present invention, the formula (3) compound, the formula (4) compound, the formula (5) compound, the formula (9) compound, and the formula (10) compound, which were described in the synthesis examples, were used. Note that the formula (9) compound is a publicly-known compound which has already been described in Patent Literature 2. In addition, as a positive control, 8-[(E)-2-(3,4-dimethoxyphenyl)vinyl]-1,3-diethyl-7-methyl-3,7-dihydro-1H-purin-2,6-dione (KW-6002) described in Patent Literature 1, which is an adenosine $A_{2a}$ receptor antagonist which has conventionally been deemed to have an effect on the treatment of Parkinson's syndrome, and the compound of the following formula (hereinafter referred to as "AT-compound"), which is shown in Patent Literature 3, compound No. 9 in [Table A], were used.

[Formula 9]

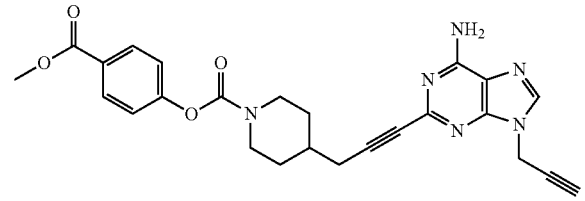

Evaluation Results:

As shown in FIG. 1, compared with KW-6002 or the AT-compound used as a positive control, the compound of the present invention has been shown to inhibit the relaxing action induced by $A_{2a}$ receptor agonist YT-146 in a concentration-dependent manner, in addition, remarkably strongly, that is, to have an extremely potent activity as an adenosine $A_{2a}$ receptor antagonist compared with the conventional compounds.

Of these, the formula (4) compound, the formula (5) compound, and the formula (10) compound exhibit a more potent activity even compared with the formula (3) compound and the formula (9) compound, and therefore it has been suggested that such compounds have bromo or furyl at position 8 and thereby have the adenosine $A_{2a}$ receptor antagonist activity remarkably potentiated, and thus have a extremely potent antagonist activity.

Example 3

Evaluation of the Binding Affinity of the Compound of the Present Invention to Human Adenosine $A_{2a}$ Receptor by Binding Assay Evaluation Method:

In order to clarify the binding affinity of the compound of the present invention to a human adenosine $A_{2a}$ receptor, a binding assay for the human receptor and the compound of the present invention was conducted. As a test substance, the formula (4) compound, which is one of the compounds which have been shown to have an adenosine $A_{2a}$ receptor antagonist activity in the above Example 2, was used, and as a positive control, a publicly-known adenosine $A_{2a}$ receptor agonist, 2-P-(2-carboxyethyl)phenethylamino-5'-N-ethylcarboxyamide adenosine hydrochloride (hereinafter referred to as "CGS21680 hydrochloride") was used.

In addition, as other conditions for the assay, 50 mM Tris-HCl (pH7.4) containing 10 mM magnesium chloride, 1 mM EDTA and 2 unit/mL adenosine deaminase were used for a buffer, CGS21680 hydrochloride was used as a displacer, and CGS21680 hydrochloride [dipropyl-2,3-3H(N)] was used as a tracer. The protocol was according a publicly-known method (The Journal of Pharmacology and Experimental Therapeutics, Vol. 323, No. 2 708-719, or the like), and the reaction time was set at 90 minutes at 25° C. The assay was performed 3 times, and based on the results of the reaction, the Ki value of the compound of the present invention was calculated.

TABLE 1

| Compound name | Ki value | Standard error |
| --- | --- | --- |
| Formula (4) compound | $5.81 \times 10^{-10}$ | $4.01 \times 10^{-11}$ |
| CGS21680 hydrochloride | $2.71 \times 10^{-8}$ | $3.05 \times 10^{-9}$ |

Evaluation Results:

As shown in the above Table 1, the compound of the present invention has been found to exhibit a strong binding affinity to a human adenosine $A_{2a}$ receptor.

In addition, Non-Patent Literature 2 shows the Ki value of the publicly-known compound described in Patent Literature 1, 8-[(E)-2-(3,4-dimethoxyphenyl)vinyl]-1,3-diethyl-7-methyl-3,7-dihydro-1H-purin-2,6-dione (KW-6002), for an adenosine $A_{2a}$ receptor to be $9.12 \times 10^{-9}$, and compared with the results of the above Table 1, it has been suggested that the compound of the present invention may have a higher binding affinity than that of KW-6002.

Example 4

Evaluation of the Therapeutic Effect of the Compound of the Present Invention on Haloperidol-Induced Catalepsy Evaluation Method:

Haloperidol is known to block dopamine receptors. This method is used generally as a method of evaluating the therapeutic effect of the therapeutic agents for Parkinson's syndrome, by using the effect of inducing catalepsy (when being made to take a certain posture or position of the limbs extrinsically, continuing to keep the posture as it is without willing to change it by oneself) caused by administration of haloperidol.

The experiment was conducted by using 7 male ddY mice, 5-weeks old, per group. Haloperidol was suspended in 0.5% CMC, and then administered intraperitoneally to the mice at 1 mg/kg. In the study, as a test compound, the compounds each represented by the formula (4), the formula (5), the formula (10), the formula (11), the formula (12), the formula (13), or the formula (14) in the above synthesis examples were used, and as a positive control, KW-6002 (the test compound and KW-6002 were 0.03, 0.1, 0.3, 1, 3, 10 mg/kg) or L-DOPA (100 mg/kg)+benserazide (25 mg/kg) was used. The above 4 compounds were each suspended in 0.5% CMC, and orally administered to the mice 1 hour after the haloperidol administration. In addition, the case where only CMC was administered was designated as a control for the whole. After a lapse of 1, 3, 5, and 7 hours from the administration of the test compound, both forelimbs only, or both hindlimbs only, of a mouse were put in turn on an acrylic stand, height 4.5 cm, width 1.0 cm, and catalepsy was determined, and the state was scored as Table 2 below.

TABLE 2

| | |
|---|---|
| Score 0 | For each case where the forelimbs and the hindlimbs are put on the stand, the holding time of the posture in which the relevant limbs remain put on the stand is less than 5 seconds. |
| Score 1 | The posture in which the forelimbs remain put on the stand is kept for 5 seconds or more, but less than 10 seconds, and for the hindlimbs the holding time is less than 5 seconds. |
| Score 2 | The posture in which the forelimbs remain put on the stand is kept for 10 seconds or more, and for the hindlimbs the holding time is less than 5 seconds. |
| Score 3 | (1) Both for the forelimbs and the hindlimbs, the holding time of the posture in which the relevant limbs remain put on the stand is 5 seconds or more, but less than 10 seconds, or (2) the holding time of the posture in which the forelimbs remain put on the stand is less than 5 seconds, and for the hindlimbs the holding time is 5 seconds or more. |
| Score 4 | (1) The posture in which the forelimbs remain put on the stand is kept for 10 seconds or more, and for the hindlimbs the holding time is 5 seconds or more, but less than 10 seconds, or (2) the posture in which the forelimbs remain put on the stand is kept for 5 seconds or more, but less than 10 seconds, and for the hindlimbs the holding time is 10 seconds or more. |
| Score 5 | Both for the forelimbs and the hindlimbs, the holding time of the posture in which the relevant limbs remain put on the stand is 10 seconds or more. |

Figure 2:
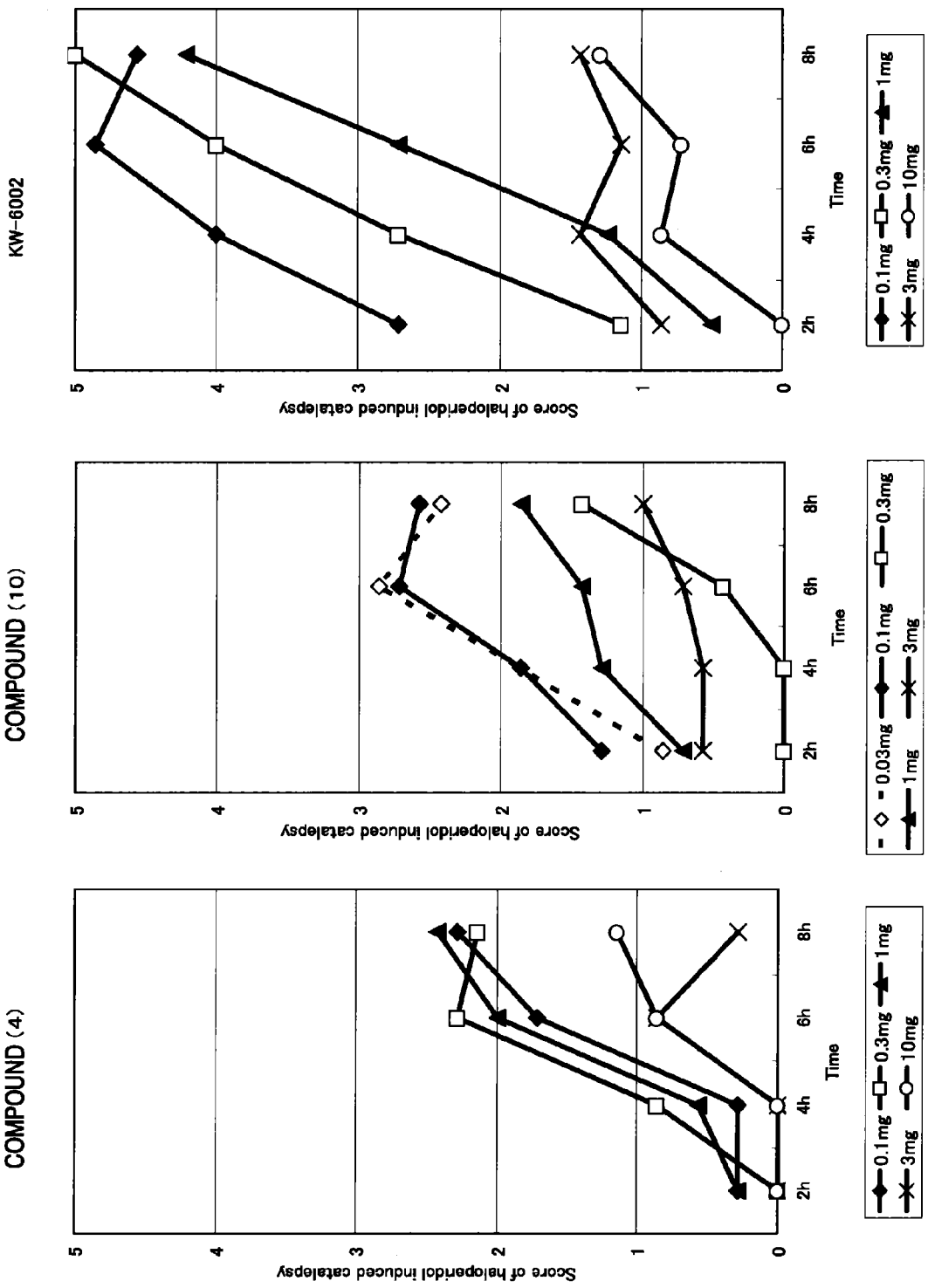
FIG. 2 shows the improving effect on haloperidol-induced catalepsy of the formula (4) compound or the formula (10) compound shown in the synthesis examples, and the positive control KW-6002. The vertical line represents the intensity degree of catalepsy, and the horizontal line represents the dose of each compound.

Evaluation Results:

As shown in FIG. 2, the formula (4) compound and the formula (10) compound in the present invention kept the score of catalepsy low, with a smaller dose than that of KW-6002 used as a positive control, in addition, for a long time, that is, had an effect of improving from lowering the motor function in haloperidol-induced catalepsy. Thus, the compound of the present invention can be considered to be, as a therapeutic agent for Parkinson's syndrome, a compound more promising than KW-6002.

Figure 3:
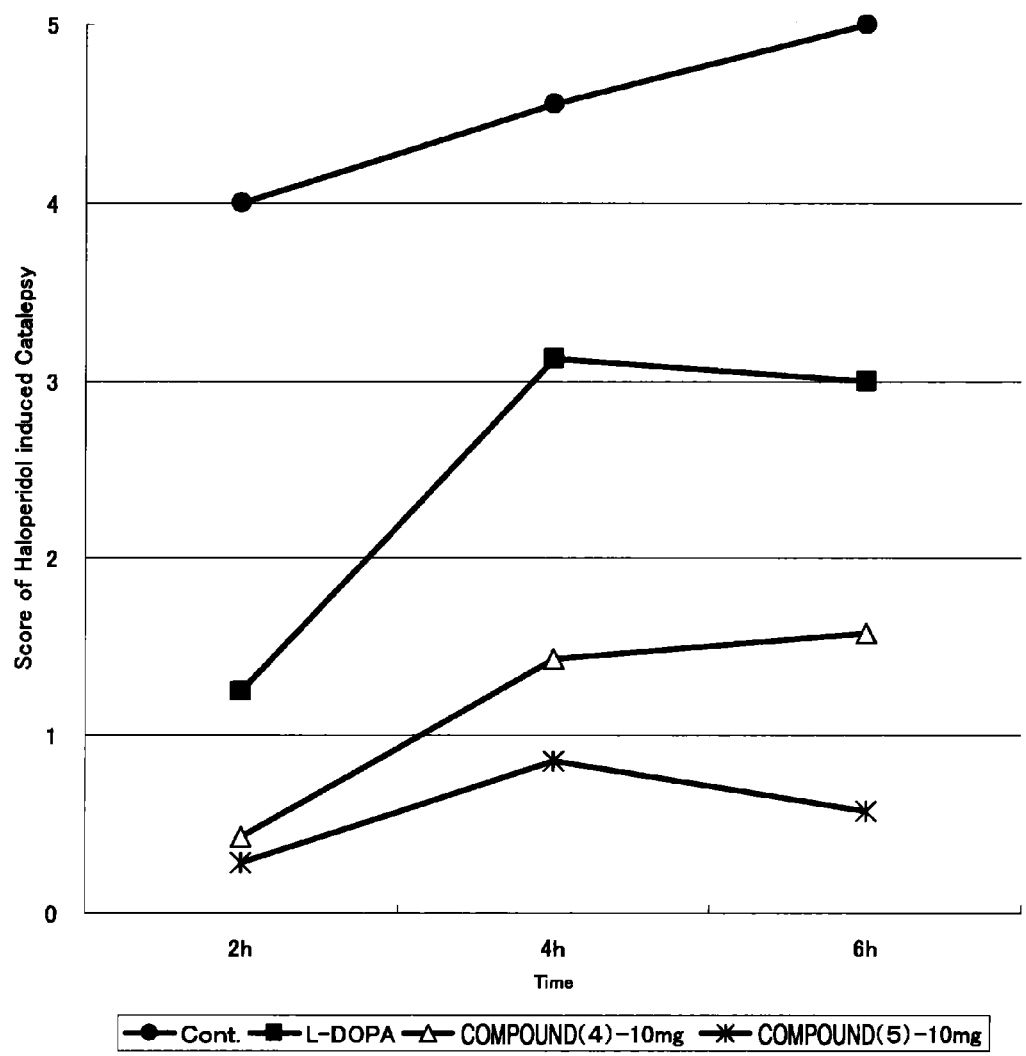
FIG. 3 shows the improving effect on haloperidol-induced catalepsy of the formula (4) compound or the formula (5) compound shown in the synthesis examples, and L-DOPA. The vertical line represents the intensity degree of catalepsy, and the horizontal line represents the time after the administration.

In addition, as shown in FIG. 3, when the formula (5) compound was administered, the catalepsy score was also kept low compared with that of L-DOPA or the formula (4) compound, and accordingly it has been suggested that this compound is promising as a therapeutic agent for Parkinson's syndrome as well.

Figure 4:
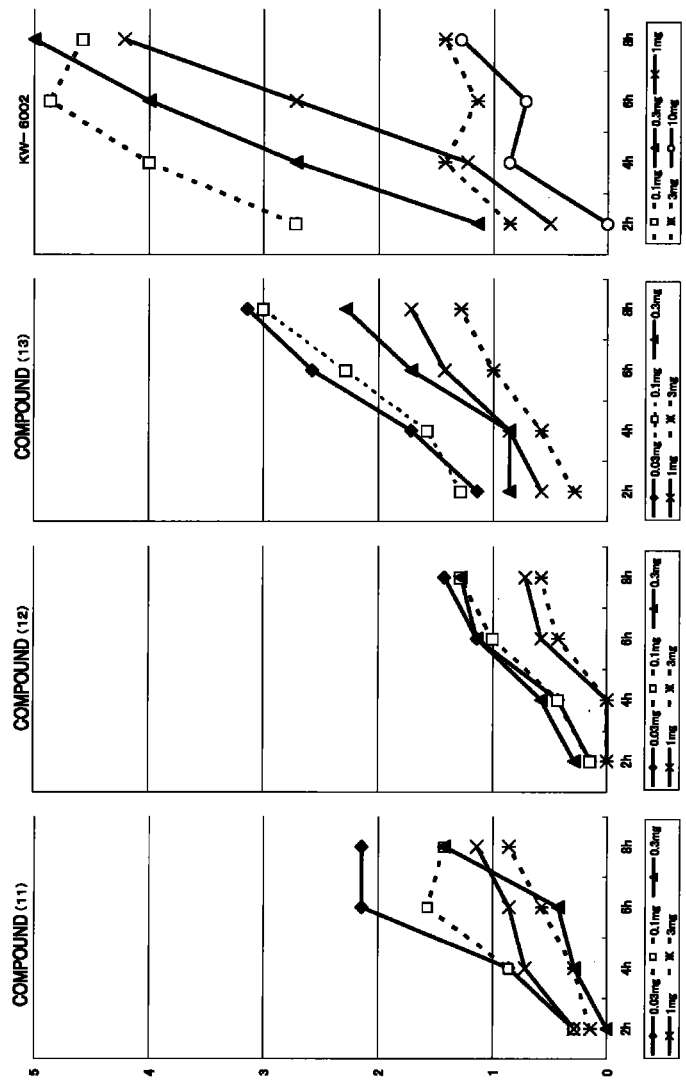
FIG. 4 shows the improving effect on haloperidol-induced catalepsy of the formula (11) compound, the formula (12) compound, or the formula (13) compound shown in the synthesis examples, and the positive control KW-6002. The vertical line represents the intensity degree of catalepsy, and the abscissa represents the dose of each compound.

Furthermore, as shown in FIG. 4, the formulae (11), (12), (13), and (14) compounds also exhibit an effect for a long time, with a smaller dose than that of the positive control KW-6002, and thus it has been suggested that these compounds are also promising as a therapeutic agent for Parkinson's disease.

Example 5

The Analysis of the Action of the Compound of the Present Invention in 6-OHDA-Induced Unilaterally Substantia Nigra Lesioned Rats 6-Hydroxydopamine (6-OHDA) is taken into neurons by dopamine reuptake transporters and acts as a neurotoxin, and is used for the selective denaturation and removal of dopaminergic neurons. This 6-OHDA was locally administered to the corpus striatum to induce the cell death of dopaminergic nerve and reduce dopamine, and thereby induce the symptoms of Parkinson's syndrome. In the study, 6-OHDA was injected into the right ventral tegmental area of male SD rats, 8-weeks old, and after 4 weeks, apomorphine (5 mg/kg, s.c.) was administered, and the animals which had shown a certain count of the counterclockwise rotation were selected. Using the model rats, the evaluation of the test compound as a therapeutic agent for Parkinson's syndrome was commenced.

(1) Preparation Method of A Unilaterally Substantia Nigra Lesioned Rat

Male SD rats, 8-weeks old, were anesthetized with pentobarbital (50 mg/kg), and the hairs were removed broadly from the occiput through the back of the neck, and then an ear bar was attached thereto, and the rats were fixed in a brain stereotaxic apparatus. The skin of the head was incised 3 to 4 cm with a scalpel, the periosteum was stripped off to expose the skull and the suture was checked. After the coordinate measurement, a hole was made in the skull with an electric drill, and a microinjection cannula was inserted 5.0 mm beneath the brain surface. 6-OHDA was dissolved in a 0.02% ascorbic acid saline solution so as to be 3.5 mg/ml, and the solution was administered at 4 points in the brain at 2 μl/2 minutes. After the administration, the rat was left for 1 minute, and a similar operation was performed for the 4 points. After the completion of the administration, an antibiotic was applied and the incised part was sutured. 4 weeks after the 6-OHDA administration, apomorphine (5 mg/kg, s.c.) was administered, and the count of the counterclockwise rotation for 5 minutes was counted from 5 minutes after the administration. The individuals which made 7 rotations or more for 1 minute were selected as a unilaterally substantia nigra lesioned rat, and used for the evaluation thereafter.

(2) Method of the Behavior Observation

As a test compound, the formula (4) compound and the formula (10) compound in the synthesis examples were used, and as a positive control, KW-6002 was used. These test compounds were orally administered to the unilaterally substantia nigra lesioned rats, singly or in combination with L-DOPA. Immediately after the administration, the rats were placed in the center of an observation box (70 cm×70 cm×30 cm), and the behavior observation was performed by using a video tracking system (Muromachi Kikai Co., Ltd.), setting 15 minutes as 1 session, for a total of 5 hours (20 sessions), and thus the count of the contralateral rotation was counted. Note that when the test compound has an effect as a therapeutic agent for Parkinson's syndrome, the count of the contralateral rotation will increase.

(3) Results

Figure 5:
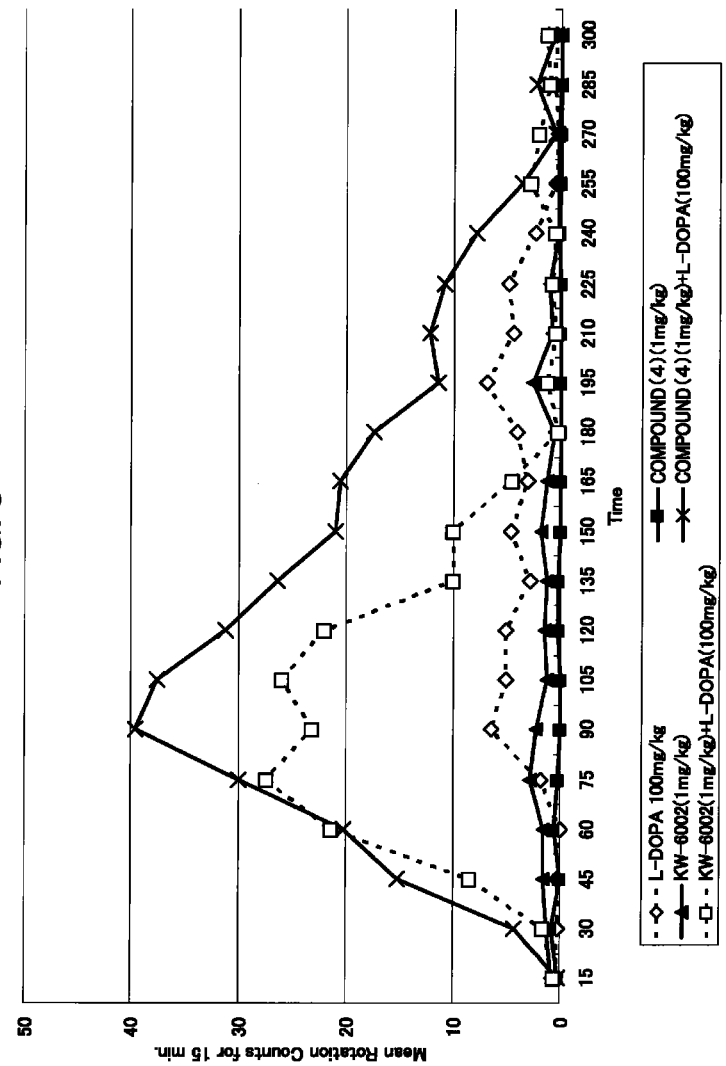
FIG. 5 shows the results of the analysis of the action, in 6-OHDA-induced unilaterally substantia nigra lesioned rats, of the formula (4) compound shown in the synthesis examples, or the positive control KW-6002, administered singly or in combination with L-DOPA. The horizontal line represents the time after the administration of the test compound (min), and the vertical line represents the mean rotation count per 15 minutes in the rats.
Figure 6:
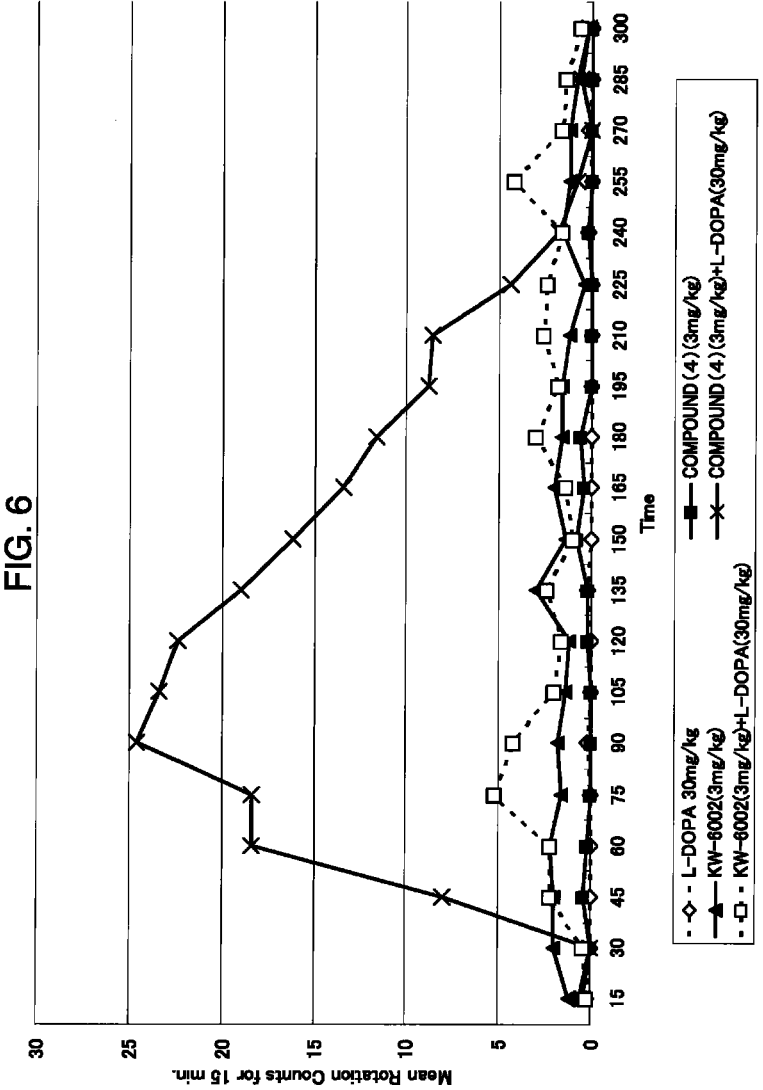
FIG. 6 shows the results of the analysis of the action, in 6-OHDA-induced unilaterally substantia nigra lesioned rats, of the formula (4) compound shown in the synthesis examples, or the positive control KW-6002, administered singly or in combination with L-DOPA.
Figure 7:
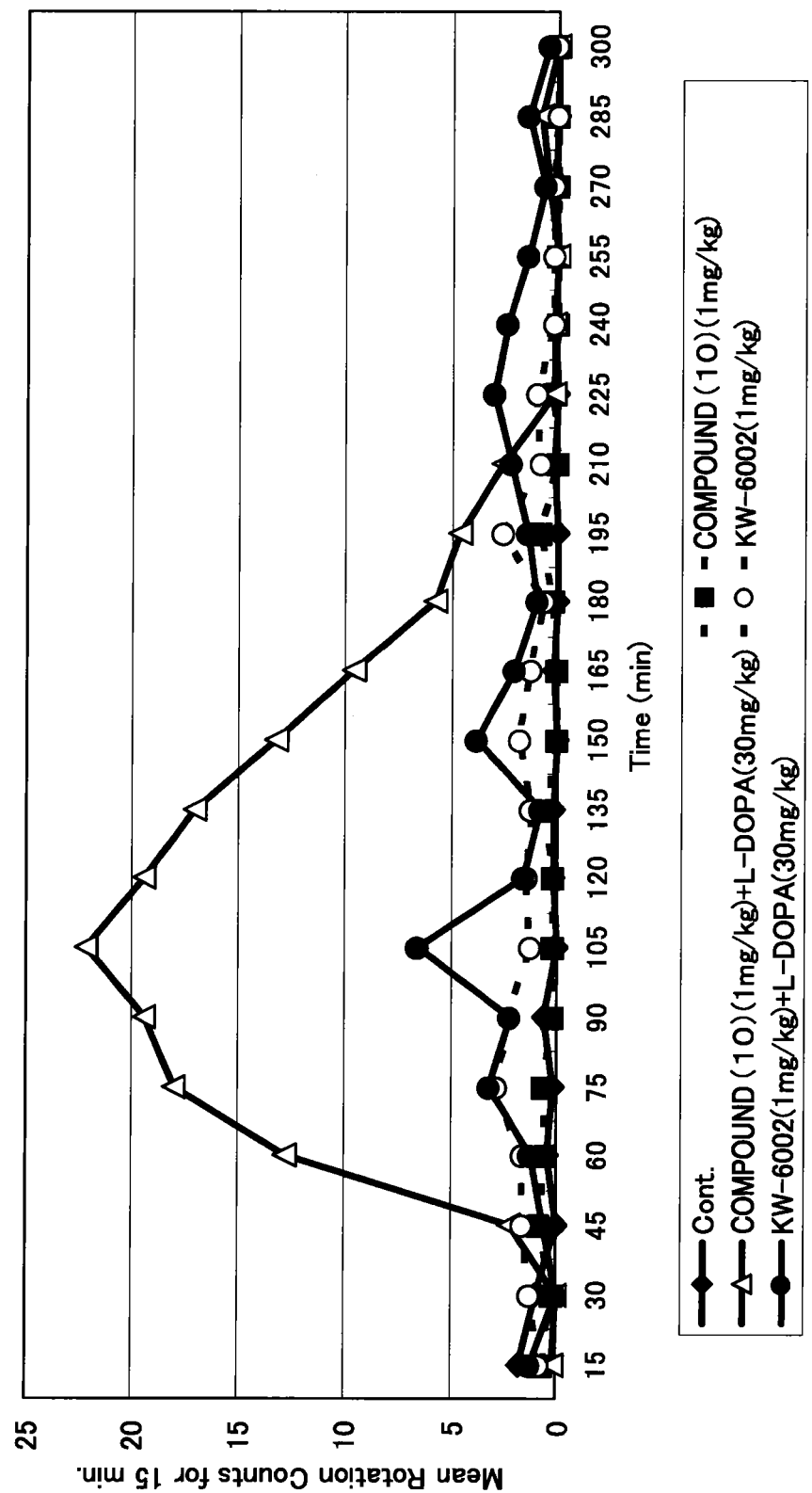
FIG. 7 shows the results of the analysis of the action, in 6-OHDA-induced unilaterally substantia nigra lesioned rats, of the formula (10) compound shown in the synthesis examples, or the positive control KW-6002, administered singly or in combination with L-DOPA. The horizontal line represents the time after the administration of the test compound (min), and the vertical line represents the mean rotation count per 15 minutes in the rats.

As shown in FIGS. 5 to 7, compared with the case where KW-6002, used a positive control, was administered singly, the formula (4) compound and the formula (10) compound of the present invention have been found to exhibit an effect which is stronger and continuously increase the count of the contralateral rotation, and have a strong effect as a therapeutic agent for Parkinson's syndrome. Moreover, the administration of the compound of the present invention in combination with L-DOPA further increased the count of the contralateral rotation, and accordingly the combination has proved to have a therapeutic effect on Parkinson's syndrome.

From the results shown in the above, compared with KW-6002 or the AT-compound, which has conventionally been expected as a therapeutic agent for Parkinson's syndrome, the compound of the present invention has been found to exhibit a remarkable effect, with a smaller amount, on the improvement of Parkinson's syndrome, and furthermore be able to maintain the effect for a long time.

Example 6

Photostability Study on the Compound of the Present Invention

Of the compounds of the present invention, the formula (4) compound, the formula (10) compound, and the formula (11) compound were evaluated for their photostability in solid state.

The study was conducted in accordance with "Guideline for the Photostability Testing of New Drug Substances and Products." That is, each compound in solid state was placed under a fluorescent light statically for 3 weeks, and the residual ratio was calculated from the HPLC analysis results before and after the placement. As a result, the residual ratio for the formula (4) compound, the formula (10) compound and the formula (11) compound was 99.0%, 98.8%, and 100.2%, respectively, and accordingly all of the compounds were found to have sufficient photostability.

INDUSTRIAL APPLICABILITY

The compound of the present invention has high chemical stability, especially high photostability, and compared with previously reported therapeutic agents for Parkinson's syndrome as an adenosine $A_{2a}$ receptor antagonist, the compound of the present invention exerts an effect with a smaller dose, in addition, for a long time, and is extremely useful as a therapeutic agent for Parkinson's syndrome. Moreover, the combination of the compound of the present invention with L-DOPA, the efficacy of which has conventionally been known to be lowered by long-term administration, can be expected to provide a stronger improving effect on symptoms, and moreover, can be expected to control the lowering of the efficacy of L-DOPA by long-term use.

The invention claimed is:

1. A compound represented by formula (I):

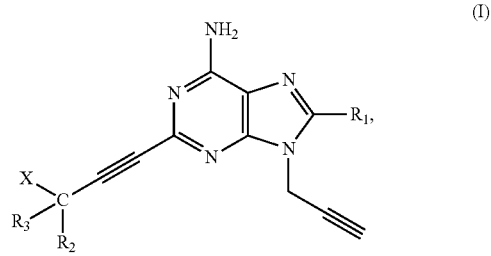

wherein:
$R_1$ represents halogen, a furyl group or a triazolyl group;
$R_2$ and $R_3$ independently represent hydrogen or an alkyl group having 1 to 8 carbon atoms, or $R_2$ and $R_3$ represent a cycloalkyl group in which $R_2$ and $R_3$ are linked together; and
X represents hydrogen or a hydroxyl group,
or a pharmaceutically acceptable salt thereof.

2. The compound or a pharmaceutically acceptable salt thereof according to claim 1, wherein $R_1$ is bromo or chloro.

3. The compound or a pharmaceutically acceptable salt thereof according to claim 1, wherein $R_1$ is a 2-furyl group or a 2-triazolyl group.

4. The compound or a pharmaceutically acceptable salt thereof according to claim 1, wherein:
$R_2$ is hydrogen; and
$R_3$ is an alkyl group having 1 to 8 carbon atoms.

5. The compound or a pharmaceutically acceptable salt thereof according to claim 1, wherein $R_2$ and $R_3$ are a cycloalkyl group in which $R_2$ and $R_3$ are linked together.

6. The compound or a pharmaceutically acceptable salt thereof according to claim 1, which is 8-bromo-2-alkynyl-$N^9$-propargyladenine or 8-chloro-2-alkynyl-$N^9$-propargyladenine.

7. The compound or a pharmaceutically acceptable salt thereof according to claim 1, which is 8-(2-furyl)-2-alkynyl-$N^9$-propargyladenine or 8-(1,2,3-triazol-2-yl)-2-(1-alkynyl)-$N^9$-propargyladenine.

8. The compound or a pharmaceutically acceptable salt thereof according to claim 1, which is 8-bromo-2-(1-hydroxycycloalkypethynyl-$N^9$-propargyladenine, or 8-chloro-2-(1-hydroxycycloalkyl)ethynyl-$N^9$-propargyladenine.

9. The compound or a pharmaceutically acceptable salt thereof according to claim 1, which is 8-(2-furyl)-2-(1-hydroxycycloalkyl)ethynyl-$N^9$-propargyladenine or 8-(1,2,3-triazol-2-yl)-2-(1-hydroxy cycloalkyl)ethynyl-$N^9$-propargyladenine.

10. A pharmaceutical composition comprising the compound or a pharmaceutically acceptable salt thereof according to claim 1, and a pharmaceutically acceptable carrier.

11. The pharmaceutical composition according to claim 10, which is suitable as an adenosine $A_{2a}$ receptor antagonist.

* * * * *